United States Patent [19]

Kiimalainen et al.

[11] Patent Number: 4,994,158
[45] Date of Patent: Feb. 19, 1991

[54] METHOD FOR ANALYZING A GAS MIXTURE

[75] Inventors: Jorma Kiimalainen; Risto J. A. Helke, both of Tampere, Finland

[73] Assignee: Oy Tampella AB, Finland

[21] Appl. No.: 196,548

[22] Filed: May 20, 1988

Related U.S. Application Data

[63] Continuation-in-part of Ser. No. 859,823, May 5, 1986, abandoned, which is a continuation-in-part of Ser. No. 668,963, Nov. 7, 1984, Pat. No. 4,586,390, and a continuation-in-part of Ser. No. 669,007, Nov. 7, 1984, abandoned.

[30] Foreign Application Priority Data

Nov. 17, 1983 [FI] Finland .................. 834,209
Nov. 17, 1983 [FI] Finland .................. 834,210

[51] Int. Cl.$^5$ .................. G01N 27/333
[52] U.S. Cl. .................. 204/153.1; 73/23.2; 73/28.01; 204/153.15; 204/409; 204/416; 422/88; 436/79
[58] Field of Search ....... 204/1 T, 4 A, 409, 416–420, 204/153.1, 153.15; 73/23, 28, 23.2, 28.01; 422/88; 436/79

[56] References Cited

U.S. PATENT DOCUMENTS

| | | | |
|---|---|---|---|
| 1,994,884 | 3/1935 | Chew | 255/1 |
| 2,682,277 | 6/1954 | Marshall et al. | 137/334 |
| 3,198,265 | 8/1965 | Voelkerding | 173/74 |
| 3,559,491 | 2/1971 | Thoen | 73/421.5 |
| 3,786,682 | 1/1974 | Winter et al. | 73/421 B |
| 4,032,395 | 6/1977 | Burnette | 176/19 LD |
| 4,044,612 | 8/1977 | Powell | 73/341 |
| 4,117,714 | 10/1978 | Goodson et al. | 73/23 |
| 4,355,539 | 10/1982 | Schatz | 73/863.11 |
| 4,392,387 | 7/1983 | Izumi | 73/863.11 |
| 4,479,379 | 10/1984 | Tarcy | 73/863.21 |

FOREIGN PATENT DOCUMENTS

| | | | |
|---|---|---|---|
| 2542962 | 5/1977 | Fed. Rep. of Germany | 73/28 |
| 1006965 | 3/1983 | U.S.S.R. | 73/863.11 |
| 714898 | 9/1954 | United Kingdom | 422/88 |

Primary Examiner—T. Tung
Attorney, Agent, or Firm—Roylance, Abrams, Berdo & Goodman

[57] ABSTRACT

The invention relates to a method for analyzing a gas mixture which contains a dust-like solid by separating and directing to analysis a certain quantity of the gas mixture along a sample-taking conduit, wherein a known quantity of liquid is mixed with the separated gas mixture in order to absorb the gas mixture into the liquid. The analysis is performed by analyzing the liquid which has absorbed the gas mixture. The liquid is mixed with the separated gas mixture which is being directed to analysis immediately after the gas mixture has been separated, and the separated gas mixture and the liquid are directed together along the sample-taking conduit to analysis.

13 Claims, 3 Drawing Sheets

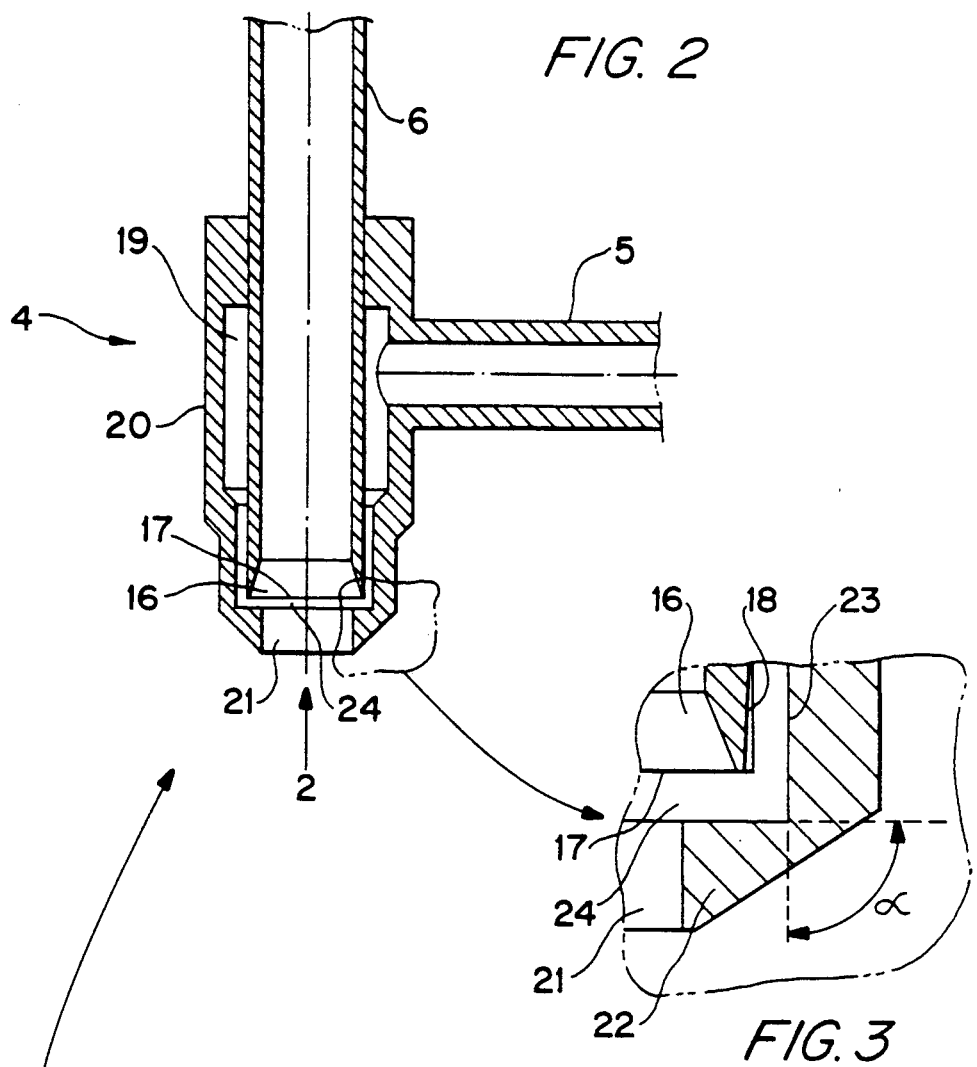
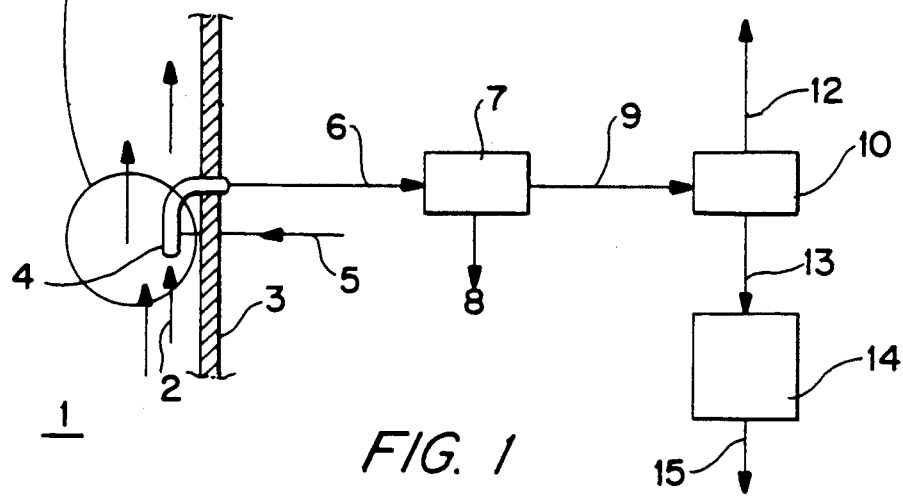

METHOD FOR ANALYZING A GAS MIXTURE

RELATED APPLICATIONS

This application is a continuation-in-part application of Ser. No. 859,823, filed May 5, 1986, now abandoned, and entitled "A Method for Analyzing a Gas Mixture", which in turn is a continuation-in-part application of Ser. No. 668,963, entitled "A Nozzle for the Continuous Separation of a Representative Sample from a Dust-Bearing Gas for its Analysis", now U.S. Pat. No. 4,586,390, and of Ser. No. 669,007, entitled "A Method for Analyzing a Gas Mixture", now abandoned, both filed Nov. 7, 1984.

BACKGROUND OF THE INVENTION

The present invention relates to a method for analyzing a gas mixture which contains a dust-like solid, by separating and directing to analysis a certain quantity of the gas mixture along a conduit for sample-taking, a method wherein a known quantity of liquid is mixed with the separated gas mixture in order to absorb the gas mixture into the liquid, and the analysis is performed by analyzing the liquid which has absorbed the gas mixture.

It is previously known to measure the dust content of flue gases by taking a sample from the flue gases at suitable intervals and by analyzing the dust content of this sample.

It is also known to measure the dust content of flue gases continuously by photo-optics, which, however, yields data which only approximately indicate the change in the dust amount.

From German Patent Application No. 27 23 310 there is, furthermore, known a method and apparatus for continuous analysis of gas by absorbing gas into a flowing liquid and by measuring by means of an ion-sensitive electrode the ions absorbed from the gas into the liquid, wherein the absorption liquid is mixed in the form of a fine mist with the gas just before the measuring, the liquid phase is separated from the gas and directed as a continuous flow through a measuring vessel equipped with an ion-specific electrode.

However, it is not possible to analyze dust-bearing gases by means of this prior known method and apparatus. In the apparatus the sample gas must travel dry over the entire length of the sample-taking pipe to the absorption point; in practice this would be a distance of several meters. In such a situation, during the measuring any dust will accumulate on the walls of the conduit, from which it must, when the quantity and components of the dust are being measured, be washed into the sample for analysis, in which case it will cause flow disturbances in the sample taking, for example, preventing the realization of the isokinetic nature of the sample taking.

In the method in the publication, the absorption takes place in a liquid spray, in which case the retention of the sample gas in the absorption is quite short and the absorption surface area is quite small, and the absorption is thus carried out very incompletely. In this case it is not possible to measure the quantitative values of the substances, and it is necessary to settle for only an indication whether or not some substance is possibly present in the gas mixture being measured. Furthermore, gases present in very low concentrations and gases which are absorbed poorly remain undetected, since owing to the short absorption time they do not have time to be absorbed in observable concentrations into the liquid.

The object of the present invention is to provide a method by which it is possible, even continuously, to measure both qualitatively and quantitatively the constituents of a gas mixture which contains a possibly dust-containing solid, and in particular a method for continuous measuring of the concentration of glauber salt in the flue gases from a recovery boiler.

In the description and claims of this Application, by the analysis of a gas mixture which contains a possibly dust-containing solid is meant the analysis of the gaseous constituents of the gas mixture and/or its various solid constituents which are in a dust-like form. By the gas mixture, respectively, is meant a combination which contains at minimum two gaseous substances or at minimum one gaseous substance and at minimum one solid.

SUMMARY OF THE INVENTION

According to the present invention, a small gas flow from the gas flow or large gas amount to be analyzed is separated isokinetically into a sample-taking conduit and directed to the analysis along the sample-taking conduit. Immediately after the gas flow has been separated, i.e., immediately at the mouth of the sample-taking conduit, a liquid is mixed with the gas flow by, for example, spraying the liquid into the sample-taking conduit from a slit-like conduit encircling its mouth, whereupon the liquid forms in the transverse direction of the sample-taking conduit a continuous film-like surface, being thus effectively mixed with the gas mixture flowing into the conduit. The liquid and the gas are on the one hand mixed with each other, whereupon absorption begins immediately, and on the other hand they form alternating sequences in the sample-taking conduit in such a way that the liquid forms plugs between which space is left for the gas. As the liquid and the gas in this manner flow along the sample-taking conduit, which can be tens of meters long, to the analysis apparatus, absorption has time to take place to maximal completion, while the liquid flowing along the conduit ensures that any dust-like particles are rinsed forward along the conduit and are not left on the conduit walls to block the conduit and thereby interfere with the measuring.

When the flow volume per time unit of the liquid to be mixed and the volume of gas flowing per time unit into the analysis are known, it is easy to determine, even as continuous measuring, those constituents present in the absorption liquid for which an analysis method is known, and further to make arrangements for the calculation on the basis of certain factors and on the basis of the measurement values obtained as the result of the analysis, in such a way that the result is the concentration of each component per gas volume unit.

If the measuring of a mean for a certain period is desired, the same absorption liquid can be circulated in the apparatus, in which case the concentration of the absorbed constituent in the liquid increases continuously. The total amount of the absorbed constituent, divided by the measured gas volume, will thus yield the mean concentration for the measuring period.

One application of continuous measuring of concentration is the measuring, with a continuous display, of glauber salt concentration in the flue gases from a recovery boiler. In this case, what is measured is a salt highly soluble in water, and its concentration in the water can be measured by a Na-specific electrode pair in the liquid flow.

Solids and gases are preferably separated from the water flow before its analysis, whereupon the sodium ion concentration in the water flow can be measured using a sodium ion specific electrode.

The water used as the absorption liquid is directed into the sample-taking chamber, for example the sample-taking point of the sample-taking probe, in order to ensure that the sample-taking opening remains open and in such a way that all of the water passes into the sample-taking chamber owing to the underpressure prevailing in it.

The water flow can be analyzed by means of a sodium ion selective electrode or by means of some other measuring device known per se, for example, a continuous-working flame photometer or by carrying out a turbidimetric sulfate analysis.

By the method according to the invention it is possible to follow up continuously the profile of the glauber salt concentration in the flue gases from a recovery boiler at different points of the flue-gas conduit. By means of the invention, immediate information is obtained regarding the glauber salt concentrations at different points of the conduit, and also information on, for example, the effect on the release of dusts, of the sweeping out of the flue or of the clattering of electrofilters.

The objectives and advantages mentioned above are achieved in such a way that the second conduit, for feeding liquid, includes at least one slit-like conduit part transverse to the central axis of the sample-taking mouth of the sample-taking conduit and situated around the said central axis, and from this part the liquid which keeps the mouth clean and mixes the gas is fed into the mouth transversely to the flow direction of the gas from around substantially the whole mouth. In practice this is achieved simply by fitting at the sample-taking end of the sample-taking pipe a substantially concentric sleeve, extending somewhat beyond it, and the liquid pipe is connected to this sleeve in order to feed liquid via the clearance or clearances between the sleeve and the sample-taking pipe to a point in front of the mouth of the sample-taking pipe, there extending inwards from the inner wall of that sleeve part which extends beyond the sample-taking end of the sample-taking pipe a ring-like stop oriented transversely to the gas flow, the slit-like conduit part being formed between the stop and the end of the sample-taking pipe.

The angle between the longitudinal axis of the sample-taking pipe and the ring-like stop oriented transversely to the gas flow and inwards from the inner wall of the open sleeve part which extends beyond the sample-taking end of the sample-taking pipe is preferably about 90° in relation to the gas flow, so that at the mouth of the sample-taking pipe there is formed a liquid film or liquid drop spray which covers as well as possible the entire cross-sectional area of the pipe and, owing to the suction prevailing in the sample-taking pipe, effectively mixes with the gas flow.

When measured axially, the slit between the sample-taking end of the sample-taking pipe and the ring-like stop of the sleeve, oriented against the gas flow, is preferably 0.005–0.1 mm in width, for example, approximately 0.05 mm. The slit between the sample-taking end of the sample-taking pipe and the ring-like stop must be continuous and maximally even, so that a drop spray or film which covers maximally well the cross-sectional area of the sample-taking mouth of the sample-taking pipe will be formed. The slit is preferably adjustable, for example, so that the sleeve is fitted to the sample-taking pipe in such a way that it can be transferred axially, and is then locked in place in relation to the sample-taking pipe. The sleeve and the sample-taking pipe can be locked in relation to each other by means of, for example, a locking ring or some other suitable method, while keeping a fitting plate in the slit during the locking.

The sample-taking pipe and the sleeve are preferably concentric in order to produce a symmetric slit or slit-like conduit part, and thus a maximally symmetric liquid spray in the sample-taking pipe, and between them there is preferably a continuous clearance having a ring-like cross section.

The diameter of the opening formed by the ring-like stop of the sleeve is preferably at maximum equal to the inner diameter of the sample-taking pipe, in certain cases even somewhat smaller than its inner diameter.

Liquid, under pressure, is fed into the preferably annular space between the sleeve and the sample-taking pipe via the second conduit. The longitudinal axis of the second conduit is preferably perpendicular to the longitudinal axis of the sleeve and the sample-taking pipe. Moreover, the second conduit may tangentially intersect with the annular space.

DESCRIPTION OF THE DRAWINGS

FIGS. 1 and 5 depicts schematically a gas analysis apparatus, provided with a nozzle, for carrying out the method according to the invention, FIG. 2 depicts a cross-sectional side view of the probe of FIG. 1, on a larger scale, FIG. 3 is a cross-sectional partial representation of the probe of FIG. 2, on a slightly still larger scale.

FIG. 5 illustrates schematically a second apparatus for carrying out the method according to the invention, as applied to the measuring of the concentration of glauber salt in a recovery boiler.

DESCRIPTION OF THE PREFERRED EMBODIMENTS

Figure 5:
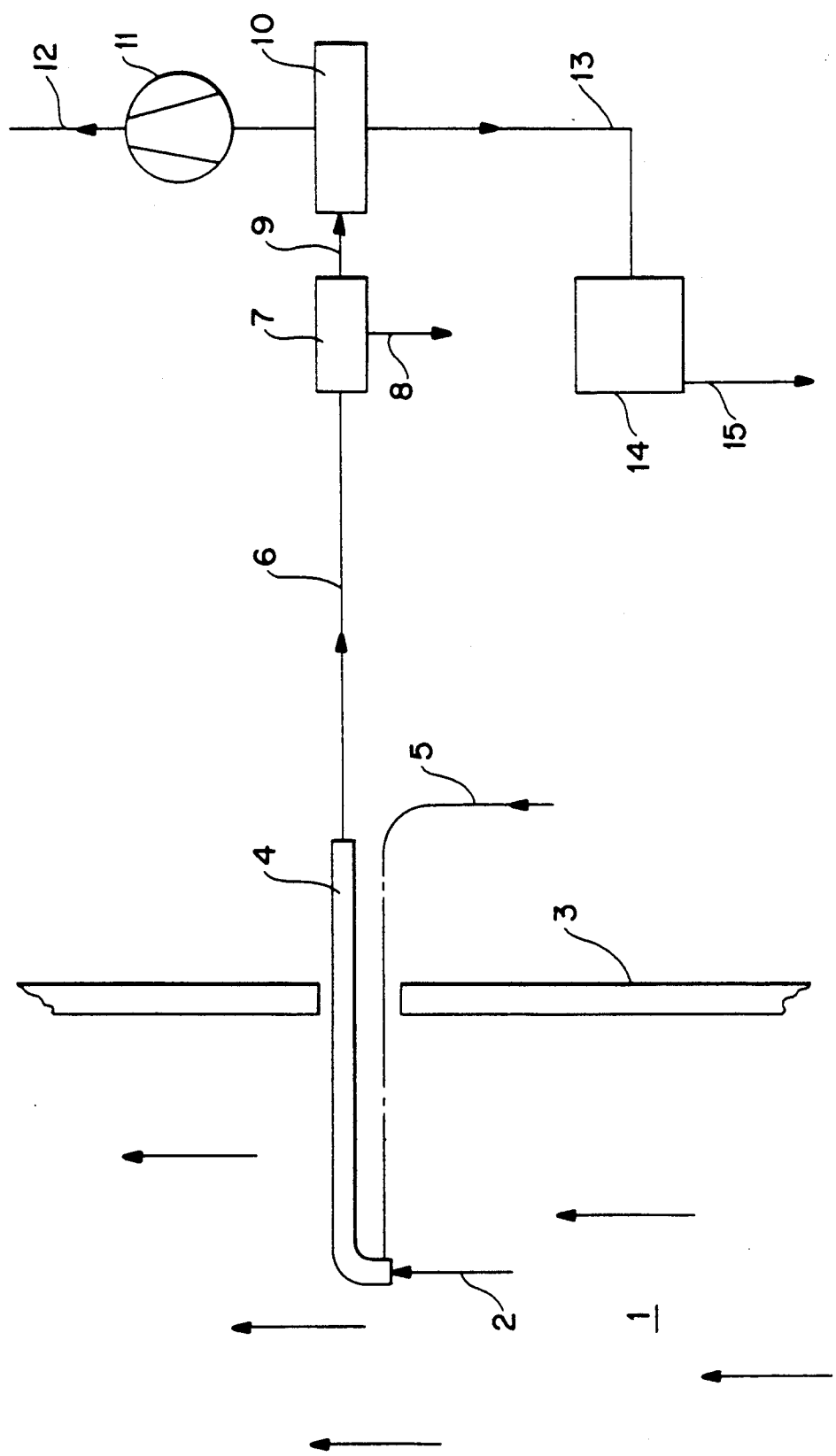

In FIGS. 1 and 5, the flue gas conduit is indicated by reference numeral 1. Sample gas 2 is sucked at a certain rate through a specific sample-taking probe 4. The interior surface of the probe is rinsed with a continuous water spray, the water being directed via pipe 5 to the sample-taking end of the sample-taking probe 4, so that all of the water passes inside the sample-taking probe 4 in order to wash the sample gas with water and to rinse the interior surface of the probe with a precisely measured amount of water, which is thereafter directed along pipe 6 to a separating device 7, in which solid particles 8 insoluble in water are separated from the water flow 9, which is directed into the subsequent separating device 10, in which the gases 12 are separated from the water flow 13 and pumped away by means of a pump 11. The water flow 13 is directed to a measuring cell 14, in which the concentration of sodium ions is measured continuously by means of a sodium ion specific electrode. The concentration of sodium ions as electrode potential is observed with the aid of a plotter. On the basis of the sample gas volume 2, the washing solution volume 5 and the measured sodium ion concentration it is possible to calculate the glauber salt concentration in the flue gas at each given moment. These can all be determined by well known means.

Finally, the water flow 15 is directed to a drain or returned to the process.

As is seen in greater detail in FIG. 2, the sample-taking probe, indicated in general by reference numeral 4, consists of a sample-taking pipe 6 having at its sample-taking end 17 a sample-taking mouth 16 opening into the sample-taking space. At the sample-taking end 17 of the sample-taking pipe 6 there is fitted a sleeve 20 which extends somewhat beyond it and encircles it, and to which the water pipe 5 has been connected in order to feed water into the annular clearance 19 between the sleeve 20 and the sample-taking pipe 6, and from there further, via the annular slit between the outer wall 18 of the sample-taking end 17 of the sample-taking pipe 6 and the inner wall 23 of the sleeve, to a point in front of the mouth 16 of the sample-taking pipe 6, as seen in greater detail in FIG. 3. In order to direct the water flow to a point in front of the mouth 16 of the sample-taking pipe 6, there is in that part of the sleeve which extends beyond the end 17 of the sample-taking pipe 6 a ring-like stop 22 which is oriented inwards from the inner wall 23, transversely to the gas flow, this stop 22 forming an angle with the central axis of the sample-taking mouth 16 of the sample-taking pipe 6. This angle α is 90° in the embodiment shown in the drawing, but it can be smaller or larger.

The dimension of the slit between the sample-taking end 17 of the sample-taking pipe 6 and the ring-like stop 22 of the sleeve 20 is relatively critical, and it must, when measured axially, be in the order of 0.005–0.1 mm, and preferably about 0.05 mm when water is used as the rinsing liquid.

As is seen in greater detail in FIG. 3, the diameter of the opening 21 formed by the ring-like stop 22 of the sleeve 20 is smaller than the inner diameter of the sample-taking pipe 6, a factor which is advantageous although not necessary.

As is seen in FIG. 2, the water pipe belonging to conduit 5 meets the sleeve 20 substantially perpendicularly and is preferably at the same time tangential to the sample-taking pipe 6. The nozzle according to the present invention enables a continuous quantitative analysis of dust-bearing gas to be carried out, since all of the absorption liquid used can be measured and, furthermore, it is ensured that the probe remains open. If, for example, under conditions more difficult than normal it seems that, nevertheless, the probe tends to get clogged, the sample-taking can be interrupted momentarily whereupon the water flow discharging from the slit 24, when the suction prevailing in the sample-taking pipe 6 during sample taking is interrupted, is directed outwards from the nozzle into the sample-taking space and effectively cleans the mouth 16 of the sample-taking pipe 6 and the opening 21 formed by the ring-like stop 22 of the sleeve 20. Such a short-time wash can be carried out sequentially so that the tip of the nozzle will not get soiled. When the suction of the sample into the sample-taking pipe 6 is resumed, its quality is immediately correct, since the entrance of both the gas sample and of the washing liquid into the sample-taking pipe 6 have been interrupted during the above-mentioned sequential cleaning.

In terms of the functioning of the invention it is advantageous that the liquid is sprayed into the nozzle at a point as close as possible to the front edge of the nozzle so that the part of the sample-taking conduit which tends to get soiled will be as short as possible. For this reason it is advantageous to make the stop 22 of the sleeve 20 as thin as possible in the axial direction, at least at that edge which is towards the sample-taking mouth.

By means of the invention described above, a nozzle is obtained wherein, inside the sample-taking pipe, there is formed, as close as possible to the sample inlet, a liquid film against which the gas and the dust contained in the gas impinge and immediately begin to dissolve in the liquid.

After passing through the nozzle, when flowing with the gas in the pipe 6, the washing liquid forms plugs appearing at rather regular intervals and thus rinses the pipe walls well, forming a large absorption surface for the gas and the solid contained in it.

According to FIGS. 2 and 3, there is, between the sleeve 20 and the sample-taking pipe 6, an annular clearance 19, along which the liquid is fed to a point in front of the nozzle. In practice the nozzle can also be constructed so that on the outer surface of the sample-taking pipe or on the inner surface of the sleeve there are longitudinal grooves which extend to the tip of the sample-taking pipe or to the stop of the sleeve. In this case, when the sleeve is in place, there would not be any annular clearance between the nozzle and the sleeve, but there would be only longitudinal conduits.

The diameter of the longitudinal conduits is preferably carefully selected so that the slit 24 still has a throttling effect on the water passing through slit 24. Stated differently, the conduits are preferably designed such that the water pressure in the conduits is less than in slit 24 so that throttling of the water in slit 24 is greater than the throttling of the water in the longitudinal conduits. This assures that slit 24 will deliver an unbroken "film" of water into pipe 6.

It is possible to construct the nozzle also in other ways. Instead of the sleeve structure it is possible to use, for example, the solution according to FIG. 4.

Figure 4:
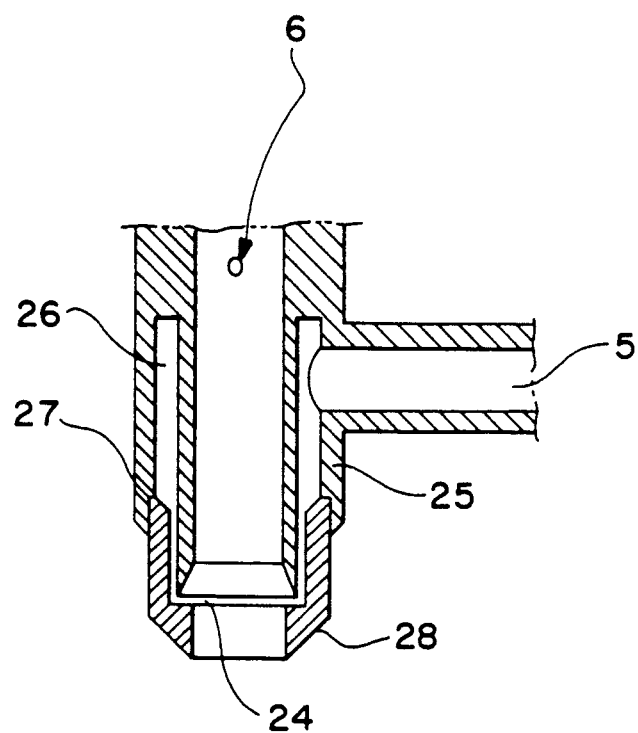
FIG. 4 depicts one embodiment of the probe according to the invention.

FIG. 4 shows part of the nozzle end, the nozzle frame being indicated by numeral 25. The nozzle frame has a sample-taking conduit 6 which runs all the way to the front of the frame. Around the sample-taking conduit 6 at the front end of the frame 25 there is formed an annular groove 26, to which the conduit 5, directing the rinsing and absorbing substance, is connected. At the front end of the frame there is installed a threaded cap-like piece 28, which is attached to the frame 25 either on the circumference of the frame or, as in FIG. 4, by means of threading provided in the ring-like groove 26. In this case the clearance of the nozzle, i.e., the axial width of the slit 24, can be easily set by shaping the cap-like pieces in such a way that they have a fixed mating surface which engages the frame at, for example, the mating surface of the frame at the point indicated by 27 and, respectively, a limiting surface 29 coming in alignment to the slit 24 situated at some distance in relation to the mating surface in the axial direction. By making the axial distance between the mating surface and the limiting surface 29 different in the different pieces 28, the clearance can be adjusted easily without any precise measuring work, when the difference between the distance between the mating surface in the frame and the end surface of the frame, and respectively the mating surface of the cap-like piece and the limiting surface in each piece, are known.

The operation of the nozzle according to the invention can under some conditions be further improved by placing one or several slit-like conduit parts 24 successively in the axial direction of the sample-taking conduit, in which case the corresponding number of liquid films are produced, which promotes mixing. In this case it is also possible to use narrower slits and thus thinner water films. Instead of the ring-like slit 24 it is, of course, also possible to use a slit which forms a gently rising spiral which encircles the sample-taking mouth at least once. Thereby a continuous liquid film which covers the cross-sectional area of the conduit is formed, as seen in the axial direction of the sample-taking conduit. When using a spiral slit it is possible, by using a suitable structure and a suitable material, to adjust the width of the slit by compressing or stretching the spiral in the axial direction. In the variations depicted above it is, of course, preferable that the first slit, or the beginning of the spiral slit, is as close as possible to the edge of the sample-taking mouth so that the edge will not get considerably soiled.

Slit-like conduit parts 24 can also be combined, for example, by fitting first a ring-like conduit part and thereafter a spiral-like conduit part, or vice versa, or in some other way. The parts of the conduit can be parallel to each other in such a way that the water films formed have the same orientation in relation to the central axis of the nozzle. The slit-like conduit parts can also have different orientations in relation to each other, in which case the water films are respectively in different orientations in relation to the central axis.

A use of this invention in a typical environment, the analyzing of the flue gas from a recovery boiler, is as follows.

Gas flow in the flue of a recovery boiler can vary depending on many factors. For purposes of this example, it will be assumed that the gas velocity in the flue is approximately 10 meters per second, a typical velocity. The sample from the gas flow to be analyzed is taken into sample-taking probe isokinetically. If sample-taking probe 4 has an interior diameter of approximately six millimeters, this will result in a gas flow of approximately one cubic meter per hour in probe 4, assuming that the temperature of the gas in the flue to be approximately 160° C. and that the gas contains approximately 20% steam by volume. The temperature of the gas will cool as the gas passes through sample-taking probe 4 and pipe 6. The gas may cool to a temperature of about 20° C. to 40° C., at which time the gas will be flowing at a rate of approximately 0.5-0.6 cubic meters per hour. Thus, the gas flow in sample-taking probe 4 and pipe 6 may vary between 0.5-1.0 cubic meters per hour. The preferred water flow for such an environment is between 6-10 liters per hour. This water is of course directed into the sample-taking end of sample-taking probe 4 via pipe 5.

At these gas and liquid flow rates, the ratio between the water volume flow to the average volume flow of the gas is approximately 1:100 (using the liquid flow rate in the middle of the range, 8 liters per hour and an average gas flow rate of 0.8 cubic meters per hour).

This ratio results in the formation of liquid plugs in sample-taking probe 4. That is, the ratio of liquid volume to gas volume is such that plugs of liquid which completely fill the cross section of the probe 4 will be formed and travel with the gas flow in the probe 4. The formation of these liquid plugs is discussed in detail in *Chemical Engineer's Handbook*, Fifth Edition, copyright 1973, by Perry and Hilton, at pages 5-40 through 5-47. The formation of the liquid plugs is a natural phenomenon which occurs at known liquid to gas volume ratios in pipes such as disclosed herein.

Also, this range of liquid flow results in the formation of a thin film at the inlet of sample-taking probe 4. The formation of this film wets the entire circumference of the surface of probe 4. In addition, the film has such a low energy that the gas flow directs all the water inside the sample-taking probe 4.

Moreover, employment of a liquid flow in this range will ensure that (1) the liquid will form liquid plugs (and not an aerosol) which move readily from the inlet of sample-taking probe 4 to the outlet of pipe 6, (2) a real solution is formed having a suitable concentration of salts to enable measuring the salt quantity, (3) the liquid does not create large pressure drops in the sample-taking probe 4, and (4) the liquid flow is sufficient to prevent the hot gas from evaporating the liquid.

The invention is in no way limited to the example presented above, but it is applicable to all kinds of gas analysis, for example, examination of the pollution of city air and of the accumulation of various substances and gas constituents, or their continuous follow-up in, for example, places in which a certain constituent or certain constituents may have a significant effect.

What is claimed is:

1. A method for analyzing a gas mixture which contains a finely divided solid which comprises, separating a predetermined quantity of said gas mixture from said gas mixture by introducing said predetermined quantity of said gas mixture into a first open end of a sample-taking conduit, concurrently introducing a predetermined quantity of liquid in which said finely divided solid is dissolvable substantially at said first open end of said sample-taking conduit with said predetermined quantity of said gas mixture to form a mixture of said predetermined quantity of said gas mixture and said predetermined quantity of said liquid in which at least a portion of said finely divided solids become dissolved into said liquid and at least a portion of the dissolvable components of said gas mixture become absorbed into said liquid, said liquid being concurrently introduced into said sample-taking conduit in such a manner that plugs of said liquid are formed between which space is left for the gas, passing said predetermined quantity of said gas mixture and said predetermined quantity of liquid through said sample-taking conduit for a time sufficient to enable substantially complete absorption of the absorbable components of said predetermined quantity of said gas mixture into said predetermined quantity of liquid, the flowing predetermined quantity of liquid rinsing the walls of said conduit and preventing deposits of said finely divided solids on said conduit walls, and withdrawing said predetermined quantity of liquid from a second open end of said sample-taking conduit and passing said predetermined quantity of liquid to an analysis zone to determine the absorbed constituent concentration of said predetermined quantity of liquid.

2. A method according to claim 1, further comprising the step of providing means at said first open end for introducing said liquid such that said liquid forms a continuous film transverse to the gas flow.

3. A method according to claim 1, further comprising the step of providing a conduit in the shape of a slit which encircles the first open end through which the liquid is introduced into the sample-taking conduit.

4. A method according to claim 1, wherein the step of introducing said liquid is conducted such that said liquid forms a continuous film transverse to the gas flow.

5. A method according to claim 1, in which in order to mix a continuously determined flow volume of the separated gas mixture with liquid, said liquid has a predetermined flow volume and is fed continuously into the sample-taking conduit in order to carry out continuous analysis.

6. A method according to claim 1, in which a predetermined quantity of liquid is circulated for a predetermined time period by recycling analyzed liquid into the sample-taking conduit in order to analyze the gas mixture accumulation during said time period.

7. A method according to claim 1, in which solids which have not been dissolved in said liquid and gases which have not been absorbed into said liquid are separated from said liquid before passing said liquid to said analysis zone.

8. A method according to claim 1, further comprising the step of recirculating said predetermined quantity of liquid at least once through the first open end and the sample-taking conduit after the step of withdrawing said predetermined quantity but before the step of passing said predetermined quantity to analysis.

9. A method according to claim 1, in which the liquid fed in is maintained at a substantially constant temperature.

10. A method according to claim 1 for the analysis of the concentration of glauber salt in the flue gases from a recovery boiler in which the liquid used is water and that the sodium concentration in the water is measured by means of a sodium-specific electrode.

11. A method according to claim 1, in which said predetermined quantity of liquid is introduced into said sample-taking conduit and mixed with the separated gas mixture by spraying it into said sample-taking conduit to form a film in a transverse direction in said sample-taking conduit.

12. A method according to claim 1, in which said predetermined quantity of said gas mixture is separated from said gas mixture isokinetically into said sample-taking conduit.

13. A method for analyzing a gas mixture in a stream flow, the gas mixture containing a finely divided solid, the method comprising the steps of:

separating a first predetermined quantity of the gas mixture from the stream flow by introducing the predetermined quantity into a first open end of a sample-taking conduit, concurrently introducing a predetermined quantity of liquid substantially at the first open end of the sample-taking conduit to form a combined mixture of the gas mixture and the liquid, all of the liquid being received within the conduit, the liquid and the gas mixture being introduced into the conduit such that plugs of the liquid are formed, the gas mixture being received between the plugs of the liquid, passing the combined mixture through the sample-taking conduit for a time sufficient to enable complete absorption of components of the gas mixture into the liquid, rinsing the walls of the conduit with the plugs of liquid, and withdrawing the predetermined quantity of liquid from a second open end of the sample-taking conduit and passing the predetermined quantity of liquid to apparatus for analyzing the liquid to determine the solid which has been absorbed into the liquid, based, in part, on the predetermined quantity of liquid and the rate of the stream flow.

* * * * *